United States Patent [19]

Gayer et al.

[11] Patent Number: 4,921,993
[45] Date of Patent: May 1, 1990

[54] SUBSTITUTED BENZAMIDE FUNGICIDES

[75] Inventors: Herbert Gayer, Monheim; Klaus Jelich, Wuppertal; Wolfgang Krämer, Burscheid; Wilhelm Brandes, Leichlingen, all of Fed. Rep. of Germany

[73] Assignee: Bayer Aktiengesellschaft, Leverkusen, Fed. Rep. of Germany

[21] Appl. No.: 123,822

[22] Filed: Nov. 23, 1987

[30] Foreign Application Priority Data

Dec. 12, 1986 [DE] Fed. Rep. of Germany ....... 3642450

[51] Int. Cl.$^5$ ............................................. A01N 33/08
[52] U.S. Cl. .................................... 558/392; 558/388
[58] Field of Search ............... 558/388, 392; 548/152, 548/203, 217, 237; 549/436

[56] References Cited

U.S. PATENT DOCUMENTS

| 3,829,464 | 8/1974 | Kornus et al. | 260/471 C |
| 4,447,446 | 5/1984 | Kay | 558/392 |

FOREIGN PATENT DOCUMENTS

| 0059536 | 9/1982 | European Pat. Off. | |
| 0135304 | 3/1985 | European Pat. Off. | |
| 0156773 | 10/1985 | European Pat. Off. | |
| 1934443 | 1/1971 | Fed. Rep. of Germany | |
| 0255759 | 12/1985 | Japan | 558/392 |
| 2146983 | 5/1985 | United Kingdom | 558/392 |
| 2152927 | 8/1985 | United Kingdom | 558/392 |
| 2183639 | 6/1987 | United Kingdom | 558/392 |

Primary Examiner—William R. Dixon, Jr.
Assistant Examiner—James M. Hunter
Attorney, Agent, or Firm—Spring Horn Kramer & Woods

[57] ABSTRACT

Fungicidally active substituted benzamides of the formula

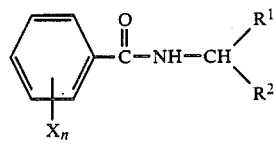

in which

R$^1$ represents alkoxy, alkenyloxy, alkinyloxy or a heterocyclyl radical,

R$^2$ represents cyano, a carbamoyl radical or a thiocarbamoyl radical,

X represents an alkanoyl radical or an alkoximinoalkyl radical, and n represents a number 1, 2 or 3.

Intermediates wherein R' is replaced by bromine and R$^2$ is cyano or a carbamoyl radical are also new.

12 Claims, No Drawings

SUBSTITUTED BENZAMIDE FUNGICIDES

The invention relates to new substituted benzamides, several processes for their preparation, and their use as pesticides.

It has already been disclosed that certain substituted amides, such as, for example, 2-(4-chlorobenzamido)-2-ethoxy-acetonitrile, have fungicidal and herbicidal properties (cf., for example, EP No. 59,536).

However, the fungicidal activity of the previously known compounds is not completely satisfactory in all areas of application, in particular at low application rates and concentrations. In addition, the herbicidal active components of the previously known compounds is often not sufficiently selective and undesired damage to the crop plants treated is produced.

New substituted benzamides of the general formula (I)

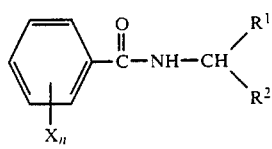

in which
  $R^1$ represents alkoxy, alkenyloxy, alkinyloxy or a heterocyclyl radical,
  $R^2$ represents cyano, a carbamoyl radical or a thiocarbamoyl radical,
  X represents an alkanoyl radical or an alkoximinoalkyl radical, and
  n represents a number 1, 2 or 3,
have been found.

It has furthermore been found that the new substituted benzamides of the general formula (I)

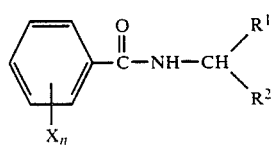

in which
  $R^1$ represents alkoxy, alkenyloxy, alkinyloxy or a heterocyclyl radical,
  $R^2$ represents cyano, a carbamoyl radical or a thiocarbamoyl radical,
  X represents an alkanoyl radical or an alkoximinoalkyl radical, and
  n represents a number 1, 2 or 3,
are obtained by one of the processes described below:
  (a) substituted benzamides of the formula (Ia)

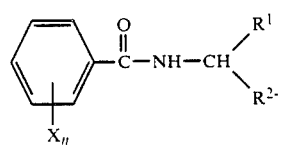

in which
  $R^1$, X and n have the abovementioned meaning, and $R^{2-1}$ represents cyano or a carbamoyl radical, are obtained when bromine-substituted benzamides of the formula (II)

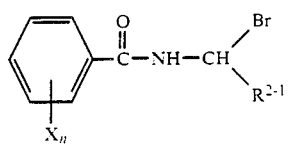

in which
  $R^{2-1}$, X and n have the abovementioned meaning, are reacted with alcohols or heterocyclic compounds of the formula (III)

$$R^1\text{—H} \qquad (III)$$

in which
  $R^1$ has the abovementioned meaning,
if appropriate in the presence of a diluent and if appropriate in the presence of an acid-binding agent;
  (b) substituted benzamides of the formula (Ib)

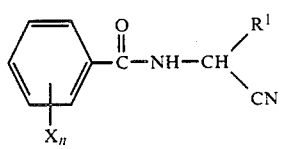

in which
  $R^1$, X and n have the abovementioned meaning, are alternatively obtained when the substituted benzamides of the formula (Ia1)

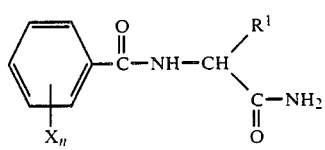

in which
  $R^1$, X and n have the abovementioned meaning, obtainable by process (a) are dehydrated using a dehydrating reagent, if appropriate in the presence of a diluent and if appropriate in the presence of an acid-binding agent;
  (c) substituted benzamides of the formula (Ic)

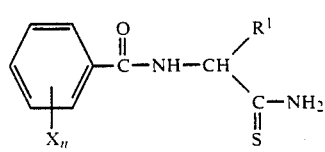

in which
  $R^1$, X and n have the abovementioned meaning, are obtained when the substituted benzamides of the formula (Ib)

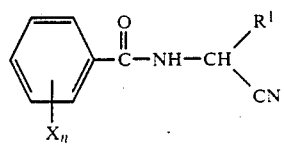

in which
R¹, X and n have the abovementioned meaning, obtainable by process (a), (b), (d) or (e) are reacted with hydrogen sulphide, if appropriate in the presence of a diluent and if appropriate in the presence of a basic catalyst;

(d) substituted benzamides of the formula (Id)

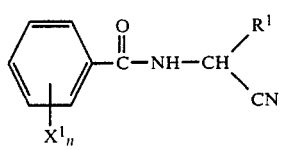

in which
R¹ and n have the abovementioned meaning, and
X¹ represents an alkoximinoalkyl radical, are alternatively obtained when the substituted benzamides of the formula (If)

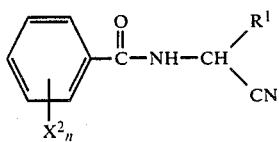

in which
R¹ and n have the abovementioned meaning, and
X² represents an alkanoyl radical, obtainable by process (a), (b) or (e) are reacted with hydroxylamine derivatives of the formula (IV)

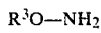

in which
R³ represents alkyl, or with the acid-addition salts thereof, if appropriate in the presence of a diluent and if appropriate in the presence of an acid-binding agent;

(e) substituted benzamides of the formula (Ie)

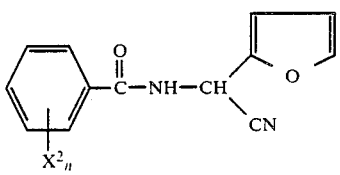

in which
X² and n have the abovementioned meaning, are alternatively obtained when substituted benzoyl chlorides of the formula (V)

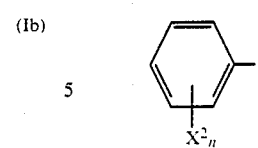

in which
X² and n have the abovementioned meaning,
are reacted with furanylaminoacetonitrile of the formula (VI)

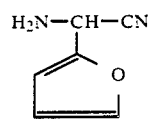

or the acid-addition salts thereof, if appropriate in the presence of a diluent and if appropriate in the presence of an acid-binding agent.

Finally, it has been found that the new substituted benzamides of the general formula (I) act against pests.

Surprisingly, the new substituted benzamides of the general formula (I) exhibit a considerably improved crop plant compatibility, with a comparably good or better fungicidal action, than the substituted amides which are known from the state of the art, such as, for example, 2-(4-chlorobenzamido)-2-ethoxy-acetonitrile, which are similar compounds chemically and regarding their action.

The formula (I) provides a general definition of the substituted benzamides according to the invention. Preferred compounds of the formula (I) are those in which R¹ represents straight-chain or branched alkoxy having 1 to 8 carbon atoms, in each case straight-chain or branched alkenyloxy or alkinyloxy in each case having 3 to 8 carbon atoms, or a 5- or 6-membered heterocyclyl radical having 1 to 4 hetero atoms, in particular nitrogen, oxygen and/or sulphur, R² represents cyano, a carbamoyl radical or a thiocarbamoyl radical, X represents a straight-chain or branched alkanoyl radical having 1 to 6 carbon atoms, or a straight-chain or branched alkoximinoalkyl radical having 1 to 6 carbon atoms in each of the individual alkyl parts, and n represents a number 1, 2 or 3.

Particularly preferred compounds of the formula (I), are those in which

R¹ represents straight-chain or branched alkoxy having 1 to 6 carbon atoms, in each case straight-chain or branched alkenyloxy or alkinyloxy in each case having 3 to 6 carbon atoms, or a 1-pyrazolyl, 1-imidazolyl, 1-(1,2,4-triazolyl), 1-tetrazolyl or 2-furyl radical, R² represents cyano, a carbamoyl radical or a thiocarbamoyl radical, X represents a straight-chain or branched alkanoyl radical having 1 to 4 carbon atoms or a straight-chain or branched alkoximinoalkyl radical having 1 to 4 carbon atoms in each of the individual alkyl parts, and n represents a number 1 or 2.

Very particularly preferred compounds of the formula (I) are those in which $R^1$ represents methoxy, ethoxy, n- or i-propoxy, n-, i-, s- or t-butoxy, allyloxy, n- or i-butenyloxy, propargyloxy, n- or i-butinyloxy, a 2-furyl radical or a 1-pyrazolyl radical, $R^2$ represents cyano, X represents formyl, acetyl or methoximinomethyl and n represents 1.

If, for example, N-(bromo-cyano-methyl)-4-methoximinomethyl-benzamide and ethanol are used as starting materials, the course of the reaction of process (a) according to the invention may be represented by the following equation:

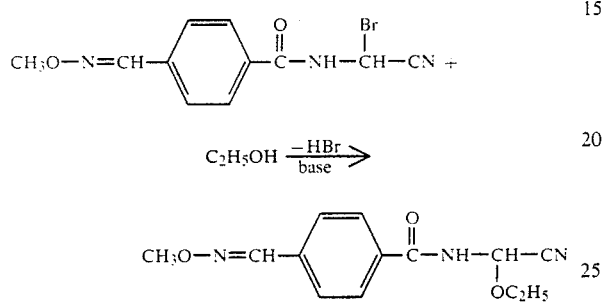

If, for example, 2-(4-methoximinomethyl-benzamido)-2-methoxy-acetamide is used as starting compound and p-toluenesulphonyl chloride is used as dehydrating agent, the course of the reaction of process (b) according to the invention may be represented by the following equation:

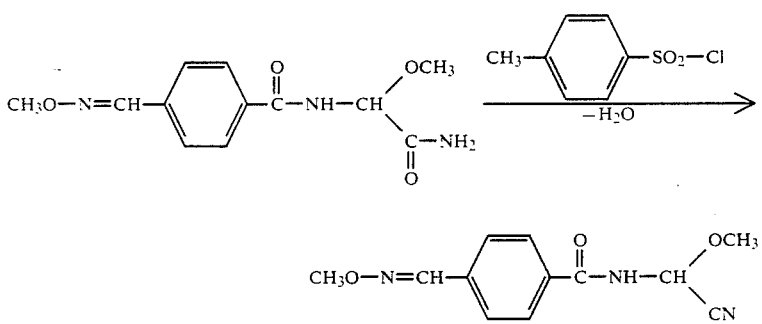

If, for example, N-(allyloxy-cyano-methyl)-4-methoximinomethyl-benzamide is used as starting compound and hydrogen sulphide is used as reagent, the course of the reaction of process (c) according to the invention may be represented by the following equation:

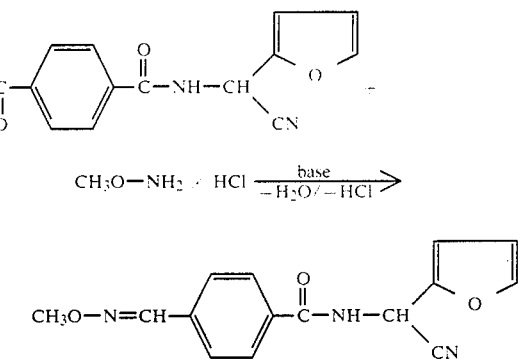

If, for example, 4-formyl-N-(cyano-2-furylmethyl)-benzamide and 0-methylhydroxylamine hydrochloride are used as starting materials, the course of the reaction of process (d) according to the invention may be represented by the following equation:

If, for example, 4-formylbenzoyl chloride and 2-amino-2-furyl-acetonitrile hydrochloride are used as starting materials, the course of the reaction of process (e) according to the invention may be represented by the following equation:

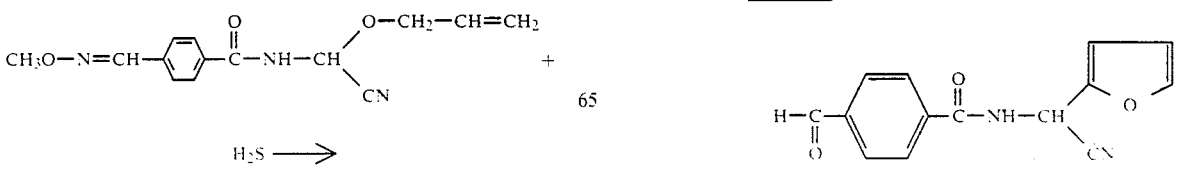

The formula (II) provides a general definition of the bromine-substituted benzamides which are required as starting materials for carrying out process (a) according to the invention. In this formula (II), X and n preferably represent those radicals and indices which have already been mentioned for these substituents or index in connection with the description of the substances of the formula (I) according to the invention.

$R^{2-1}$ preferably represents cyano or a carbamoyl radical.

The bromine-substituted benzamides of the formula (II) were hitherto not known.

They are obtained when substituted benzoyl chloride compounds of the formula (V)

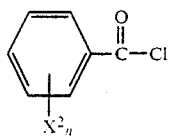

(V)

in which $X^2$ represents an alkanoyl radical, and n has the abovementioned meaning, are reacted initially in a 1st stage with α-aminoacetonitrile hydrochloride of the formula (VII)

$$H_2N-CH_2-CN \times HCl$$ (VII)

if appropriate in the presence of a diluent, such as, for example, dimethylformamide, and if appropriate in the presence of an acid-binding agent, such as, for example, triethylamine, at temperatures between −20° C. and +50° C., and the benzoylaminoacetonitriles of the formula (VIIIa)

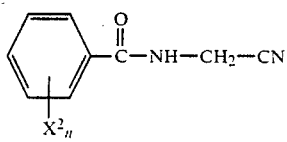

(VIIIa)

in which $X^2$ and n have the abovementioned meaning, thus obtained (a) are reacted either directly with elemental bromine, if appropriate in the presence of a diluent, such as, for example, ethyl acetate, tetrahydrofuran or acetic acid, and if appropriate in the presence of a catalyst, such as, for example, hydrobromic acid, at temperatures between −20° C. and +50° C., or (b) the compounds of the formula (VIIIa) are reacted with 0-alkylhydroxylamines of the formula (IV)

$$R^3O-NH_2$$ (IV)

in which $R^3$ represents alkyl, or with the acid-addition salts thereof, in analogy to the execution of process (d) according to the invention, if appropriate in the presence of a diluent, such as, for example, dimethylformamide, and if appropriate in the presence of an acid-binding agent, such as, for example, triethylamine, at temperatures between −20° C. and +50° C., and the benzoylaminoacetonitriles of the formula (VIIIb)

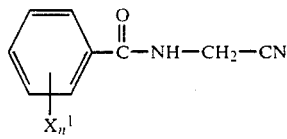

(VIIIb)

in which $X^1$ represents an alkoximinoalkyl radical, and n has the abovementioned meaning, thus obtained are reacted in a further reaction stage with elemental bromine, if appropriate in the presence of a diluent, such as, for example, ethyl acetate, tetrahydrofuran or acetic acid, and if appropriate in the presence of a catalyst, such as, for example, hydrobromic acid, at temperatures between −20° C. and +50° C.

The substituted benzoyl chloride compounds of the formula (V) are known (cf., for example, Chem. Ber. 71, 335–341 [1938]; Bull. Soc. Chem. Fr. 1970, 4452–4459; DE-OS (German Published Specification) No. 2,913,770; EP No. 153,826), or can be obtained in a simple fashion in analogy to known processes.

The α-aminoacetonitrile hydrochloride of the formula (VII) and the hydroxylamine derivatives of the formula (IV), and the acid-addition salts thereof, are generally known compounds of organic chemistry.

The formula (III) provides a general definition of the alcohols or heterocyclic compounds which are furthermore required as starting materials for carrying out process (a) according to the invention. In this formula (III), $R^1$ preferably represents those radicals which have already been mentioned for these substituents in connection with the description of the substances of the formula (I) according to the invention.

The alcohols or heterocyclic compounds of the formula (III) are generally known compounds of organic chemistry.

The formula (Ia1) provides a general definition of the substituted benzamides which are required as starting materials for carrying out process (b) according to the invention. In this formula (Ia1), $R^1$, X and n preferably represent those radicals and indices which have already been mentioned for these substituents and indices in connection with the description of the substances of the formula (I) according to the invention.

The substituted benzamides of the formula (Ia1) are compounds according to the invention and can be obtained with the aid of process (a) according to the invention.

The formula (Ib) provides a general definition of the substituted benzamides which are required as starting materials for carrying out process (c) according to the invention. In this formula (Ib), $R^1$, X and n preferably represent those radicals and indices which have already been mentioned for these substituents and indices in connection with the description of substances of the formula (I) according to the invention.

The substituted benzamides of the formula (Ib) are compounds according to the invention and can be obtained with the aid of process (a), (b), (d) or (e) according to the invention.

The formula (If) provides a general definition of the substituted benzamides which are required as starting materials for carrying out process (d) according to the invention. In this formula (If), $R^1$ and n preferably represent those radicals and indices which have already been mentioned for these substituents and indices in connection with the description of the substances of the formula (I) according to the invention.

X² preferably represents straight-chain or branched alkanoyl having 1 to 6 carbon atoms, in particular straight-chain or branched alkanoyl having 1 to 4 carbon atoms, particularly preferably formyl or acetyl.

The substituted benzamides of the formula (If) are compounds according to the invention and can be obtained with the aid of process (a), (b) or (e) according to the invention.

The formula (IV) provides a general definition of the hydroxylamine derivatives which are furthermore required as starting materials for carrying out process (d) according to the invention. In this formula (IV), R³ preferably represents straight-chain or branched alkyl having 1 to 6, in particular 1 to 4, carbon atoms, particularly preferably methyl. Suitable acid-addition salts are, in particular, hydrohalides, such as, for example, hydrochlorides or hydrobromides.

The hydroxylamine derivatives of the formula (IV) and the acid-addition salts thereof are generally known compounds of organic chemistry.

The formula (V) provides a general definition of the substituted benzoyl chlorides which are required as starting materials for carrying out process (e) according to the invention. In this formula (V), X² and n preferably represent those radicals and indices which have already been mentioned for these substituents or indices in connection with the description of the substances and precursors of the formula (If) according to the invention.

The substituted benzoyl chlorides of the formula (V) are known (cf. literature citations on p.11).

The formula (VI) provides a definition of the furanylaminoacetonitrile which is furthermore required as starting material for carrying out process (e) according to the invention.

Furanylaminoacetonitrile is known (cf. BE 833.233 of Mar. 9, 1976 or Can. PA. No. 1,063,102 of Sept. 9, 1979).

Suitable diluents for carrying out process (a) according to the invention are inert organic solvents.

These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetates, or sulphoxides, such as dimethylsulphoxide.

Process (a) according to the invention is preferably carried out in the presence of a suitable acidbinding agent. These preferably include tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (a) according to the invention, the reaction temperatures may be varied within a relatively wide range. In general, the process is carried out at temperatures between −50° C. and +100° C., preferably at temperatures between −30° C. and +50° C.

To carry out process (a) according to the invention, 1.0 to 3.0 moles, in particular 1.0 to 1.2 moles, of alcohol or heterocyclic compound of the formula (III) and 1.0 to 3.0 moles, in particular 1.0 to 2.0 moles, of acid-binding agent are generally employed per mole of bromine-substituted benzamide of the formula (II).

In a preferred method of execution, the bromine-substituted benzamides of the formula (II) used as starting materials are prepared directly in the reaction vessel in a prior reaction by brominating the appropriate cyanomethylamides of the formula (VIII)

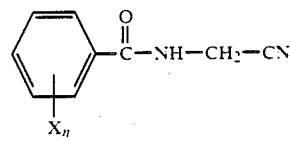

in which

X and n have the abovementioned meaning, using a suitable brominating agent, such as, for example, elemental bromine, in a suitable diluent, such as, for example, acetic acid or ethyl acetate, and if appropriate in the presence of a suitable acid catalyst, such as, for example, hydrobromic acid, at temperatures between −20° C. and +20° C., and further reacting directly subsequently in a "one-pot process" according to process (a) according to the invention.

Depending on the choice of diluent and depending on the acid concentration, either simultaneous hydration of the nitrile group to form the corresponding amides of the formula (IIa)

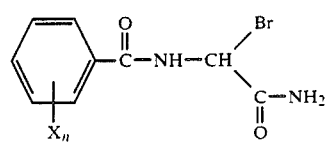

in which

X and n have the abovementioned meaning, or amides of the formula (IIb)

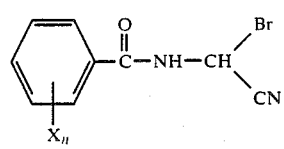

in which

X and n have the abovementioned meaning, in which the nitrile group is retained as such are obtained in this prior bromination reaction (cf. EP Nos. 59,536, 135,304 and the preparation examples).

Process (a) according to the invention and the workup and isolation of the reaction products of the formula (Ia) are carried out in analogy to known processes (cf. EP No. 59,536).

Suitable dehydrating agents for carrying out process (b) according to the invention are all conventional dehydrating agents. Acid chlorides or acid anhydrides, such as, for example, trifluoroacetic anhydride, p-toluenesulfonyl chloride, trichloroacetyl chloride, methanesulfonyl chloride, titanium tetrachloride or phosphorus oxychloride, are used with particular advantage.

Suitable diluents for carrying out process (b) according to the invention are likewise inert organic solvents.

These include, in particular, aliphatic or aromatic, optionally halogenated hydrocarbons, such as, for example, benzine, benzene, toluene, xylene, chlorobenzene, pyridine, petroleum ether, hexane, cyclohexane, dichloromethane, chloroform and carbon tetrachloride, ethers, such as diethyl ether, dioxane, tetrahydrofuran or ethylene glycol dimethyl or diethyl ether, nitriles, such as acetonitrile or propionitrile, or amides, such as dimethylformamide.

Process (b) according to the invention is, if appropriate, carried out in the presence of a suitable acid-binding agent. Suitable such agents are, in particular, tertiary amines, such as N-methylmorpholine, triethylamine, N,N-dimethylaniline, pyridine, N,N-dimethylaminopyridine, diazabicyclooctane (DABCO), diazabicyclononene (DBN) or diazabicycloundecene (DBU).

When carrying out process (b) according to the invention, the reaction temperatures may be varied within a relatively wide range. In general, the process is carried out at temperatures between $-20°$ C. and $+80°$ C., preferably at temperatures between $0°$ C. and $+40°$ C.

To carry out process (b) according to the invention, 1.0 to 5.0 moles, preferably 1.0 to 3.0 moles, of dehydrating agent are generally employed per mole of substituted benzamide of the formula (Ia1). The reaction is carried out, and the reaction products of the formula (Ib) are worked up and isolated in analogy to known processes (cf. EP No. 59,536).

Suitable diluents for carrying out process (c) according to the invention are likewise inert organic solvents. These include, in particular, the organic solvents mentioned in the case of process (a). Toluene or pyridine are used as diluents with particular advantage.

Process (c) according to the invention is preferably carried out in the presence of a basic catalyst. Suitable such catalysts are, in particular, the tertiary amines listed in the case of process (a). Triethylamine is used with particular advantage.

For carrying out process (c) according to the invention, the reaction temperatures may be varied within a relatively wide range. In general, the process is carried out at temperatures between $-20°$ C. and $+30°$ C., preferably at temperatures between $0°$ C. and $+20°$ C.

To carry out process (c) according to the invention, 1.0 to 5.0 moles, in particular 1.0 to 2.0 moles, of basic catalyst are generally employed per mole of substituted benzamide of the formula (Ib), and gaseous hydrogen sulphide is passed through the reaction solution. The reaction products of the formula (Ic) are worked up and isolated by removing precipitated solid product by filtration or by removal of the volatile components from the reaction mixture by evaporation (cf. also EP No. 59,536).

Suitable diluents for carrying out process (d) according to the invention are preferably polar organic solvents or mixtures thereof with water. In particular, dipolar, aprotic solvents, such as, for example, nitriles, such as acetonitrile or propionitrile or amides, such as dimethylformamide, dimethylacetamide, n-methylformanilide, N-methylpyrrolidone or hexamethylphosphoric triamide, if appropriate also mixed with water-miscible ethers, such as dioxane or tetrahydrofuran, or alcohols, such as methanol, ethanol or propanol, and mixtures thereof with water, are used.

Process (d) according to the invention is, if appropriate, carried out in the presence of a suitable acid-binding agent.

Suitable such agents are all conventional inorganic or organic bases. These include, for example, alkali metal hydroxides, such as sodium hydroxide or potassium hydroxide, alkali metal carbonates or acetates, such as sodium carbonate, potassium carbonate, sodium hydrogen carbonate or sodium acetate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

For carrying out process (d) according to the invention, the reaction temperatures may be varied within a relatively wide range. In general, the process is carried out at temperatures between $-20°$ C. and $100°$ C., preferably at temperatures between $0°$ C. and $80°$ C.

To carry out process (d) according to the invention, 1.0 to 1.5 moles, preferably 1.0 to 1.3 moles, of hydroxylamine derivative of the formula (IV) and, if appropriate 1.0 to 3.0 moles, preferably 1.0 to 2.0 moles, of acid-binding agent are generally employed per mole of substituted benzamide of the formula (If). In a preferred embodiment, the substituted benzamides of the formula (If) which are required as starting materials are prepared directly in the reaction vessel in a prior reaction according to process (e) according to the invention, and they are further reacted, directly from the reaction mixture without isolation, with the hydroxylamine derivative of the formula (IV). The reaction is carried out and the reaction products of the formula (Id) are worked up and isolated in analogy to generally conventional processes (cf. also the preparation examples).

Suitable diluents for carrying out process (e) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide Process (e) according to the invention is, if appropriate, carried out in the presence of a suitable acid-binding agent.

Suitable such agents are all conventional inorganic or organic bases. These include, for example, alkali metal hydroxides, such as sodium hydroxide or potassium hydroxide, alkali metal carbonates, such as sodium carbonate, potassium carbonate or sodium hydrogen carbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

For carrying out process (e) according to the invention, the reaction temperatures may be varied within a relatively wide range. In general, the process is carried out at temperatures between $-20°$ C. and $+100°$ C., preferably at temperatures between $0°$ C. and $50°$ C.

To carry out process (e) according to the invention, 1.0 to 1.5 moles, preferably equimolar amounts, of furanylaminoacetonitrile and, if appropriate, 1.0 to 2.0 moles of acid-binding agent are generally employed per mole of substituted benzoyl chloride of the formula (V). The reaction is carried out and the reaction products of the formula (Ie) are worked up and isolated in analogy to generally known processes.

The active compounds according to the invention have an action against pests and can be employed in practice for combating undesired damaging organisms. The active compounds are suitable for use, for example, as plant-protection agents, for example as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed here with particularly good success for combating plant diseases in vegetable growing, such as, for example, against the causative organism of tomato brown rot (*Phytophthora infestans*). It should be particularly emphasized that the active compounds according to the invention not only have a protective action, but, in addition, also have curative properties.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0 001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

Preparation examples

EXAMPLE 1

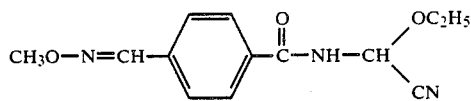

(Process a)

7.35 g (0.046 mol) of bromine and several drops of a 33 per cent hydrogen bromide solution in glacial acetic acid are added to 10 g (0.046 mol) of 2-(4-methoximinomethylbenzoyl)-amino-acetonitrile in 140 ml of ethyl acetate and 140 ml of tetrahydrofuran, and the mixture is carefully warmed. The bromination reaction sets in at about 30° C. When the reaction is complete, the mixture is cooled to −40° C. and a mixture of 9 g (0.195 mol) of ethanol, 9.3 g (0.092 mol) of triethylamine and 9 g of ethyl acetate is added. The mixture is warmed to 0° C., precipitated triethylamine hydrobromide is filtered off, and the filtrate is concentrated in vacuo. The product crystallizes from cyclohexane.

9.1 g (76% of theory) of 2-ethoxy-2-[(4-methoximinomethylbeonzoyl)-amino]-acetonitrile of melting point 143° C.–145° C. are obtained.

EXAMPLE 2:

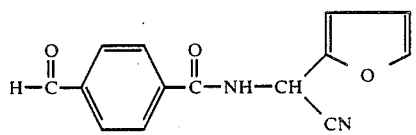

(Process e)

Firstly, 8.4 ml (0.06 mol) of triethylamine and then dropwise a solution of 5.05 g (0.03 mol) of 4-formylbenzoyl chloride in 15 ml of tetrahydrofuran are added with ice cooling to 4.75 g (0.03 mol) of 2-amino-2-furylacetonitrile hydrochloride (cf. BE 833,233) in 40 ml of dimethylformamide. When the addition is complete, the mixture is stirred for 16 hours at room temperature, then poured into ice water and extracted with ethyl acetate. The combined organic phases are washed with saturated aqueous sodium chloride solution, dried over sodium sulphate and concentrated in vacuo. The oil remaining is purified by chromatography (silica gel/dichloromethane).

3.4 g (45% of theory) of 2-[(4-formylbenzoyl)amino]-2-furylacetonitrile are obtained as an oil.

$^1$H-NMR (CDCl$_3$/tetramethylsilane): $\delta$=6.35 (d) ppm.

EXAMPLE 3:

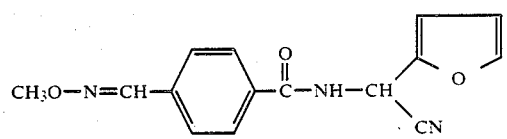

(Process d/process e "one-pot reaction")

First, 6.0 g (0.0593 mol) of triethylamine and subsequently dropwise a solution of 5.0 g (0.0297 mol) of 4-formylbenzoyl chloride in 15 ml of tetrahydrofuran are added with ice cooling to 4.7 g (0.0297 mol) of 2-amino-2-furyl-acetonitrile hydrochloride in 50 ml of dimethylformamide. When the addition is complete, the mixture is stirred for 15 minutes at room temperature and 2.5 g (0.0299 mol) of O-methylhydroxylamine and 3.0 g (0.0297 mol) of triethylamine are then added successively, and the mixture is stirred for a further 16 hours at room temperature. For work-up, the reaction mixture is poured into water and extracted repeatedly with ethyl acetate. The combined organic phases are washed with water, dried over sodium sulphate and freed from solvent in vacuo. The residue is recrystallized from toluene.

4.19 g (49% of theory) of 2-furyl-2-[(4-methoximinomethylbenzoyl)-amino]-acetonitrile of melting point 143° C. are obtained.

The following substituted benzamides of the general formula (I) are obtained in a corresponding fashion and according to the general instructions for the preparation:

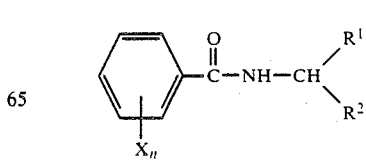

| Ex. No. | R¹ | R² | Xn | Melting point/[°C.] |
|---|---|---|---|---|
| 4 | CH₃O | CN | —C₆H₄—CH=N—OCH₃ | 117–120 |
| 5 | CH₃—(CH₂)₂—O— | CN | —C₆H₄—CH=N—OCH₃ | 115–117 |
| 6 | CH₃—(CH₂)₃—O— | CN | —C₆H₄—CH=N—OCH₃ | 104–105 |
| 7 | CH₂=CH—CH₂—O— | CN | —C₆H₄—CH=N—OCH₃ | 111–114 |
| 8 | HC≡C—CH₂—O— | CN | —C₆H₄—CH=N—OCH₃ | 101–104 |
| 9 | pyrazol-1-yl | CN | —C₆H₄—CH=N—OCH₃ | 165–167 |
| 10 | HC≡C—(CH₂)₂—O— | CN | —C₆H₄—CH=N—OCH₃ | 102–105 |
| 11 | CH₃—C≡C—CH₂—O— | CN | —C₆H₄—CH=N—OCH₃ | 76–80 |
| 12 | CH₂=CH—CH(CH₃)—O— | CN | —C₆H₄—CH=N—OCH₃ | 83–86 |
| 13 | HC≡C—CH(CH₃)—O— | CN | —C₆H₄—CH=N—OCH₃ | 81–84 |
| 14 | CH₃—CH₂—CH₂—O— | CN | —C₆H₄—CH=N—O(CH₂)₅CH₃ | 96–97 |
| 15 | HC≡C—CH₂—O— | CN | —C₆H₄—CH=N—O(CH₂)₅CH₃ | 54–56 |

-continued

| Ex. No. | $R^1$ | $R^2$ | Xn | Melting point/[°C.] |
|---|---|---|---|---|
| 16 | $H_2C=CH-CH_2-O-$ | CN | 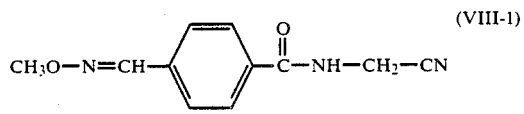—CH=N—O(CH$_2$)$_5$CH$_3$ | 78–79 |
| 17 | <img pyrazole> | CN | 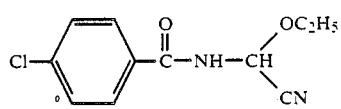—CH=N—O(CH$_2$)$_5$CH$_3$ | 121–123 |

Preparation of the starting compounds

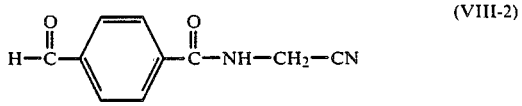
(VIII-1)
CH$_3$O—N=CH—⟨⟩—C(O)—NH—CH$_2$—CN 12.2 g (0.12 mol) of triethylamine and then, dropwise at 25° C. with stirring, 10.1 g (0.06 mol) of 4-formyl-benzoyl chloride in 10 ml of tetrahydrofuran are added at 0° C. to 5.6 g (0.06 mol) of 2-aminoacetonitrile hydrochloride in 50 ml of dimethylformamide. When the addition is complete, the mixture is stirred for 15 minutes at room temperature, and first a solution of 5 g (0.06 mol) of 0-methylhydroxylamine hydrochloride in 30 ml of dimethylformamide and then 6.1 g (0.06 mol) of triethylamine are added. The reaction mixture is then stirred for a further 12 hours at room temperature and then poured into 800 ml of ice water, and the product is filtered off, washed with water and dried.

11.5 g (88.2% of theory) of 2-(4-methoximinomethyl-benzoyl)-amino-acetonitrile of melting point 191°–193° C. are obtained.

(VIII-2)
H—C(O)—⟨⟩—C(O)—NH—CH$_2$—CN

First, 12.2 g (0.12 mol) of triethylamine and then, dropwise with stirring, a solution of 10.1 g (0.06 mol) of 4-formylbenzoyl chloride in 10 ml of tetrahydrofuran are added at 0° C. to 5.6 g (0.06 mol) of 2-aminoacetonitrile hydrochloride in 50 ml of dimethylformamide at a rate such that the internal temperature does not exceed 10° C. When the addition is complete, the batch is stirred for a further 15 minutes at room temperature, poured into 400 ml of ice water and filtered, and the product thus obtained is dried. Extraction of the filtrate with 5 times 100 ml of ethyl acetate, washing the combined organic phases, drying over sodium sulphate and concentrating in vacuo yields a further fraction. In total, 8.9 g (79% of theory) of 2-(4-formylbenzoyl)-aminoacetonitrile of melting point 122°–125° C. are obtained.

USE EXAMPLES

In the following use example, the compound shown below was employed as comparison substance:

(A)
Cl—⟨⟩—C(O)—NH—CH(OC$_2$H$_5$)(CN)

2-(4-chlorobenzoylamino)-2-ethoxy-acetonitrile (known from EP No. 59,536).

EXAMPLE A

Phytophthora Test (tomato)/curative
Solvent 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration To test for curative activity, young plants are inoculated with an aqueous spore suspension of Phytophthora infestans. The plants remain in an incubation cabin at 20° C. and 100% relative atmospheric humidity for 7 hours After a short drying-off time, the plants are sprayed with the preparation of active compound until dripping wet.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds according to Preparation Examples: 1, 4, 5 and 7.

EXAMPLE B

Plant tolerance test
Test plant: tomato
Duration of the test: 6 days
Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

Young plants are sprayed with this preparation of active compound until dripping wet and are placed in a greenhouse at about 20° C.

The plants are evaluated for damage, such as impairment of growth, discoloration and necroses.

In this test, the compound according to Preparation Example 7, for example, exhibits a clearly superior plant tolerance compared to the prior art.

It will be understood that the specification and examples are illustrative but not limitative of the present invention and that other embodiments within the spirit and scope of the invention will suggest themselves to those skilled in the art.

What is claimed is:

1. A substituted benzamide of the formula

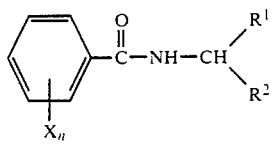

in which
R¹ represents alkoxy, alkenyloxy, alkinyloxy or a heterocyclyl radical,
R² represents cyano, a carbamoyl radical or a thiocarbamoyl radical,
X represents an alkanoyl radical or an alkoximinoalkyl radical, and
n represents a number 1, 2 or 3.

2. A substituted benzamide according to claim 1, in which
R¹ represents straight-chain or branched alkoxy having 1 to 8 carbon atoms, straight-chain or branched alkenyloxy or alkinyloxy having 3 to 8 carbon atoms, or a 5- or 6-membered heterocyclyl radical having 1 to 4 hetero atoms, and
X represents a straight-chain or branched alkanoyl radical having 1 to 6 carbon atoms or a straight-chain or branched alkoximinoalkyl radical having 1 to 6 carbon atoms in each of the individual alkyl parts.
n represents a number 1, 2 or 3.

3. A substituted benzamide according to claim 1, in which
R¹ represents straight-chain or branched alkoxy having 1 to 6 carbon atoms, straight-chain or branched alkenyloxy or alkinyloxy having 3 to 6 carbon atoms, or a 1-pyrazolyl, 1-imidazolyl, 1-(1,2,4-triazolyl), 1-tetrazolyl or 2-furyl radical,
X represents a straight-chain or branched alkanoyl radical having 1 to 4 carbon atoms or a straight-chain or branched alkoximinoalkyl radical having 1 to 4 carbon atoms in each of the individual alkyl parts, and
n represents a number 1 or 2.

4. A substituted benzamide according to claim 1, in which
R¹ represents methoxy, ethoxy, n- or i-propoxy, n-, i-, s- or t-butoxy, allyloxy, n- or i-butenyloxy, propargyloxy, n- or i-butinyloxy, a 2-furyl radical or a 1-pyrazolyl radical,
R² represents cyano,
X represents formyl, acetyl or methoximinomethyl, and n represents 1.

5. A compound according to claim 1, wherein such compound is 2-ethoxy-2-[(4-methoximinomethylbenzoyl)-amino]-acetonitrile of the formula

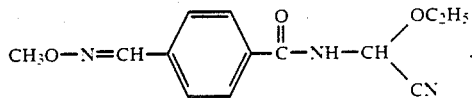

6. A compound according to claim 1, wherein such compound is 2-methoxy-2-[(4-methoximinomethylbenzoyl)-amino]-acetonitrile of the formula

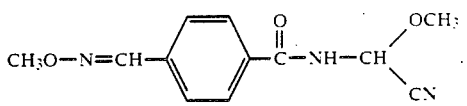

7. A compound according to claim 1, wherein such compound is 2-n-propoxy-2-[(4-methoximinomethylbenzoyl)-amino]-acetonitrile of the formula

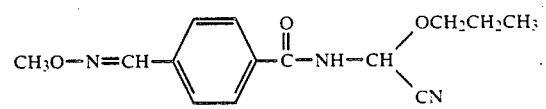

8. A compound according to claim 1, wherein such compound is 2-allyloxy-2-[(4-methoximinomethylbenzoyl)-amino]-acetonitrile of the formula

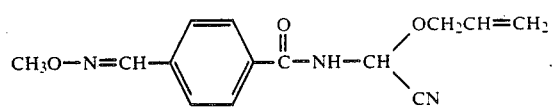

9. A fungicidal composition comprising a fungicidally effective amount of a compound according to claim 1 and a diluent.

10. A method of combating fungi which comprises applying to such fungi or to a fungus habitat a fungicidally effective amount of a compound according to claim 1.

11. The method according to claim 10, wherein such compound is
2-ethoxy-2-[(4-methoximinomethylbenzoyl)-amino]acetonitrile,
2-methoxy-2-[(4-methoximinomethylbenzoyl)-amino]acetonitrile,
2-n-propoxy-2-](4-methoximinomethylbenzoyl)-amino]acetonitrile or
2-allyloxy-2-[(4-methoximinomethylbenzoyl)amino]-acetonitrile.

12. A bromine-substituted benzamide of the formula

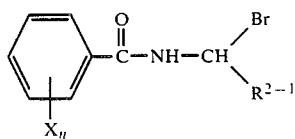

in which
R²⁻¹ represents cyano or a carbamoyl radical,
X represents an alkanoyl radical or an alkoximinoalkyl radical, and
n represents a number 1, 2 or 3.

* * * * *